United States Patent
Demri et al.

(10) Patent No.: US 9,320,474 B2
(45) Date of Patent: Apr. 26, 2016

(54) SYNCHRONIZING BETWEEN IMAGE SEQUENCES OF THE HEART ACQUIRED AT DIFFERENT HEARTBEAT RATES

(71) Applicant: BIOSENSE WEBSTER (ISRAEL) LTD., Yokneam (IL)

(72) Inventors: Tamir Demri, Gilon (IL); Ziyad Abdullatif Zeidan, Zemmer (IL); Gil Zigelman, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 283 days.

(21) Appl. No.: 14/174,933

(22) Filed: Feb. 7, 2014

(65) Prior Publication Data

US 2015/0223762 A1  Aug. 13, 2015

(51) Int. Cl.
| | |
|---|---|
| A61B 5/00 | (2006.01) |
| H04N 5/06 | (2006.01) |
| A61B 6/00 | (2006.01) |
| A61B 5/042 | (2006.01) |
| G06F 19/00 | (2011.01) |
| A61B 5/06 | (2006.01) |

(52) U.S. Cl.
CPC .............. *A61B 5/7285* (2013.01); *A61B 5/042* (2013.01); *A61B 6/487* (2013.01); *A61B 6/503* (2013.01); *A61B 6/5235* (2013.01); *A61B 6/5288* (2013.01); *H04N 5/06* (2013.01); *A61B 5/062* (2013.01); *A61B 6/468* (2013.01); *G06F 19/321* (2013.01)

(58) Field of Classification Search
CPC .................................................... A61B 5/7285
See application file for complete search history.

(56) References Cited

U.S. PATENT DOCUMENTS

| | | | |
|---|---|---|---|
| 6,389,310 B1 | 5/2002 | Demonceau | |
| 6,438,196 B1 | 8/2002 | Cesmeli | |
| 7,286,629 B2 | 10/2007 | Bruder | |
| 7,477,928 B2 | 1/2009 | Acharya | |
| 8,583,101 B1 | 11/2013 | Xu | |
| 2009/0149734 A1 | 6/2009 | Sugiura | |
| 2013/0023780 A1* | 1/2013 | Cardinale | A61B 8/0883 600/523 |
| 2013/0060156 A1* | 3/2013 | Gregg | A61B 5/04011 600/523 |
| 2013/0165781 A1* | 6/2013 | Cardinale | A61B 5/044 600/440 |

OTHER PUBLICATIONS

Bombardini, T. et al. Diastolic Time—Frequency Relation in the Stress Echo Lab: Filling Timing and Flow at Different Heart Rates. Cardiovascular Ultrasound 2008, 6:15, 1-20.
Chung, C.S. et al. Duration of Diastole and Its Phases as a Function of Heart Rate During Supine Bicycle Exercise. The American J Physiological Heart Circ. Physiol 287: H2003-H2008, 2004.

* cited by examiner

*Primary Examiner* — Peter Luong
(74) *Attorney, Agent, or Firm* — Louis J. Capezzuto

(57) ABSTRACT

A method for performing a medical procedure includes holding a non-linear dependence between the duration of a given phase within a cardiac cycle and a respective heartbeat rate. First and second image sequences of the dynamic activity of the heart of a patient, acquired at respective different first and second heartbeat rates of the heart, are received. Synchronization between the first and second image sequences is performed based on the non-linear dependence, on the first and second heartbeat rates, and on a given common heartbeat rate. The first and second image sequences are played in synchronization with the common heartbeat rate.

22 Claims, 7 Drawing Sheets

CLIP_HR < 100 BPM
MAP_HR2 < MAP_HR1 < 100 BPM

CLIP_HR > 100 BPM
MAP_HR1 > MAP_HR2 > 100 BPM

CLIP_HR < 100 BPM < MAP_HR1

MAP_HR1 < 100 BPM < CLIP_HR

SYNCHRONIZING BETWEEN IMAGE SEQUENCES OF THE HEART ACQUIRED AT DIFFERENT HEARTBEAT RATES

FIELD OF THE INVENTION

The present invention relates generally to heart imaging, and particularly to methods and systems for synchronizing between sequence images of the heart acquired at different heart rates.

BACKGROUND OF THE INVENTION

Some cardiac imaging procedures produce a clip comprising a sequence of image frames that shows the dynamic activity of the heart. Heart imaging procedures include, for example, fluoroscopic and ultrasound imaging procedures. In some cases, it is desirable to synchronize between different imaging clips. Various techniques to synchronize between separate measurements of the heart are known in the art.

For example, U.S. Pat. No. 7,477,928, whose disclosure is incorporated herein by reference, describes a method for associating ECG waveform data with computed tomography image data using a data synchronization scheme. The method includes generating the ECG waveform data using an electrocardiogram device, operating a computed tomography imaging system so as to create the computed tomography image data, communicating an exposure marker signal to the electrocardiogram device such that the exposure marker signal is associated with the EKG waveform data. The method further includes processing the computed tomography image data, the ECG waveform data and the exposure marker signal, so as to correlate the ECG waveform data with the computed tomography image data.

U.S. Pat. No. 8,583,101, whose disclosure is incorporated herein by reference, describes a method and an apparatus for synchronizing heartbeat behavior. The method includes acquiring a period list and a time list, acquiring a period length of the heartbeat behavior according to the period list, and synchronization time according to the time list, a heartbeat period, and a preset multiplier. The method further includes synchronizing at least one type of heartbeat behavior by using the period length of the heartbeat behavior as a period from the synchronization time.

U.S. Pat. No. 6,389,310, whose disclosure is incorporated herein by reference, describes the processing of data that is obtained from synchronized electrocardiogram tomoscintigraphy, said data being correlated to image giving the activity of the heart, which comprises auricles, ventricles, valves and septum. The image comprises at least first and second portions. The first portion consists of the pixels showing the auricles and ventricles during the cardiac cycle, wherein each cycle comprises successive time bins with an end-of-systole time, and end-of-diastole time. The second portion consists of pixels that are substantially not involved with the cardiac activity.

SUMMARY OF THE INVENTION

An embodiment of the present invention that is described herein provides a method for performing a medical procedure. The method includes holding a non-linear dependence between the duration of a given phase within a cardiac cycle and a respective heartbeat rate. First and second image sequences of the dynamic activity of the heart of a patient, acquired at respective different first and second heartbeat rates of the heart, are received. Synchronization between the first and second image sequences is performed based on the non-linear dependence, on the first and second heartbeat rates, and on a given common heartbeat rate. The first and second image sequences are played in synchronization with the common heartbeat rate.

In some embodiments, the common heartbeat rate equals the second heartbeat rate, synchronizing between the first and second image sequences includes synchronizing the second image sequence to the first image sequence, and playing the first and second image sequences includes playing the second image sequence in synchronization with the first heartbeat rate. In other embodiments, the given phase includes an active phase, in which a volume of a chamber of the heart changes rapidly, and holding the non-linear dependence includes holding a non-linear function that relates the duration of the active phase to the respective heartbeat rate. In yet other embodiments, the cardiac cycle further includes a passive phase in which the volume of the chamber of the heart changes slowly, and synchronizing between the first and second image sequences includes determining presentation times of images of the second image sequence in each of the active and passive phases based on the non-linear function.

In an embodiment, holding the non-linear function includes holding a piecewise linear function including two or more linear segments. In another embodiment, the piecewise linear function includes first and second linear segments corresponding to respective heartbeat rates below and above a threshold heartbeat rate. In yet another embodiment, playing the second image sequence includes selecting an image of the second image sequence whose determined presentation time matches a rendering time of a rendered image among the images of the first sequence.

In some embodiments, playing the second image sequence includes displaying the selected image of the second image sequence overlaid on the rendered image of the first image sequence. In other embodiments, receiving the first image sequence includes receiving a dynamic real-time imaging of the heart. In yet other embodiments, receiving the second image sequence includes receiving a previously recorded fluoroscopic clip.

In an embodiment, the cardiac cycle includes multiple sub-phases, the sub-phases correspond to respective multiple non-linear dependences that each relates between a duration of the respective sub-phase and the respective heartbeat rate, and synchronizing between the first and second image sequences includes determining presentation times of images of the first and second image sequences based on the multiple non-linear dependences, on the first and second heartbeat rates, and on the common heartbeat rate.

There is additionally provided, in accordance with an embodiment of the present invention, an apparatus for performing a medical procedure including an output device and a processor. The processor is configured to hold a non-linear dependence between the duration of a given phase within a cardiac cycle and a respective heartbeat rate, to receive first and second image sequences of the dynamic activity of the heart of a patient, acquired at respective different first and second heartbeat rates of the heart, to synchronize between the first and second image sequences based on the non-linear dependence, on the first and second heartbeat rates and on a given common heartbeat rate, and to play the first and second image sequences synchronized to the common heartbeat rate on the output device.

The present invention will be more fully understood from the following detailed description of the embodiments thereof, taken together with the drawings in which:

DETAILED DESCRIPTION OF EMBODIMENTS

Overview

Figure 1:
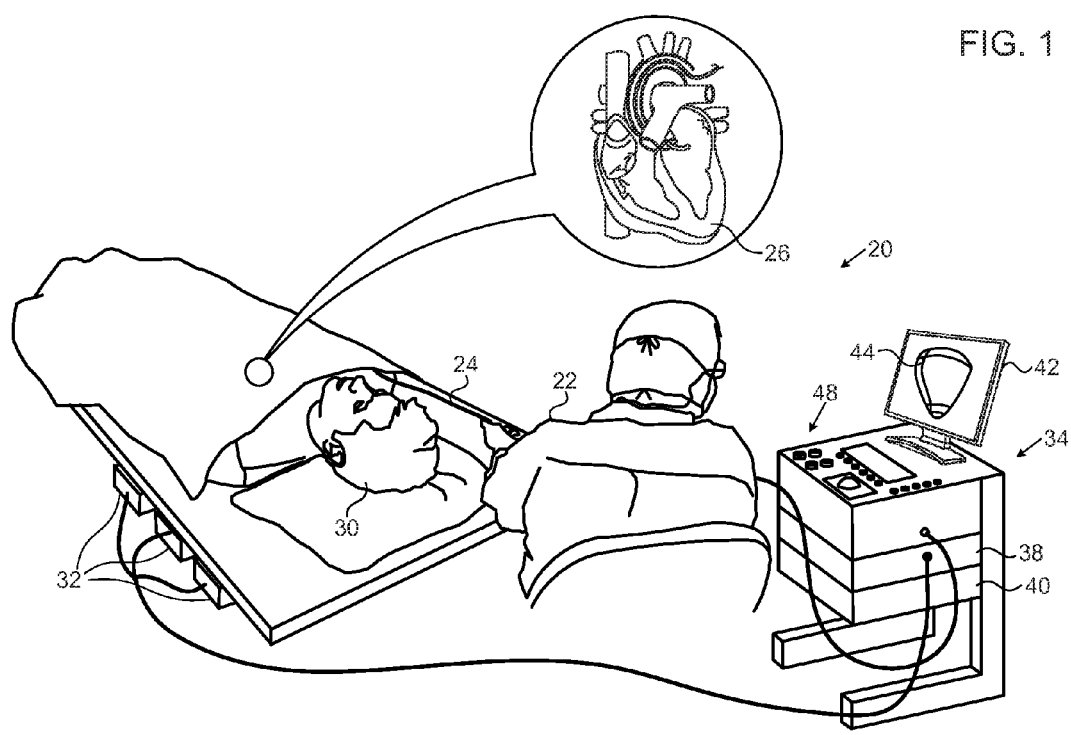
FIG. 1 is a schematic pictorial illustration of a system for intracardiac electrophysiological (EP) mapping, in accordance with an embodiment of the invention.

In some medical procedures that involve imaging or mapping of the heart, imaging is based on a catheter, which the physician inserts through the vascular system into the heart. A number of systems for cardiac mapping are commercially available, such as the CARTO™ system offered by Biosense Webster, Inc. (Diamond Bar, Calif.). CARTO tracks the position and operating parameters of the distal end of the catheter and displays this information electronically on a three-dimensional (3D) anatomical map of the heart.

During cardiac imaging, it is sometimes helpful to play a previously recorded fluoroscopic clip of the heart simultaneously with the currently produced 3D map of the heart. In the description that follows a fluoroscopic clip serves as an example for dynamic heart imaging, although any other suitable heart imaging method can also be used. Examples of other dynamic heart imaging modalities include, for example, 2D echocardiography, 3D echocardiography, Magnetic Resonance Imaging (MRI), and Computerized Tomography (CT).

In principle, it is possible to synchronize the fluoroscopic clip to the 3D map by first matching each heartbeat cycle that occurs during the current cardiac cycle to a respective clip cycle in the fluoroscopic clip, and then determining the presentation times of the clip images by linear time adjustments based on the respective cycle periods. Since, however, the fluoroscopic clip and the present cardiac mapping procedure correspond to possibly different heartbeat rates, and since the duration of intra-cycle phases within the cardiac cycle may depend differently on the underlying heartbeat rate, such a naïve synchronization scheme typically results in time-distorted synchronization, and therefore the played fluoroscopic clip fails to reflect the actual heart behavior during the present cardiac mapping.

Embodiments of the present invention that are described herein provide improved methods and systems for synchronizing image sequences of a patient heart that were acquired at different heart rates. The disclosed techniques apply non-linear time warping to one of the image sequences, in order to map it accurately onto the other sequence along the entire cardiac cycle.

In the examples described herein the disclosed techniques are used for synchronizing the playback of a fluoroscopic clip to the heartbeat rate during EP mapping of the heart. Alternatively, however, the disclosed techniques can be used to synchronize image sequences acquired using any other suitable imaging modality, including heart catheterization, transcatheter procedures, such as, for example, Atrial Septal Defect (ASD) closure, valve replacement, and biopsy of the myocardium.

In some embodiments, instead of synchronizing one image sequence to the heartbeat rate that corresponds to another image sequence, both sequences are played in synchronization with a given common heartbeat rate, which may differ from both underlying heartbeat rates corresponding to the two image sequences.

The heart cycle can be divided into an active phase in which the ventricular volume changes rapidly, and a passive phase in which the ventricular volume is static or increases slowly. Based on clinical studies, the duration of the active and passive phases depend on the underlying heartbeat rate. Below some threshold heartbeat rate (HR), the duration of the active phase is insensitive to the HR value. Additionally, above the threshold HR the passive phase vanishes and the heart cycle comprises only the active phase that shortens when increasing the HR. The threshold HR value is typically in the range of 95-105 beats per minute (BPM). In the description that follows we assume a threshold HR of 100 BPM, although any other suitable value can also be used.

In an embodiment, the dependence of the inverse multiplicative or reciprocal of the active phase duration on the HR can be approximated by a non-linear function, such as, for example, a piecewise linear function made of two linear segments. The segment below 100 BPM is close to flat and the slope of the segment above 100 BPM is unity.

In some embodiments, the synchronization of the fluoroscopic clip to the present HR is carried out in two stages. In the first stage the heart cycles occurring during the present heart mapping (also referred to herein as cardiac cycles) are matched to respective cycles of the fluoroscopic clip (also referred to as clip cycles). In the second synchronization stage, the presentation times of the clip frames within each clip cycle are time adjusted to be aligned with the full duration of the matching cardiac cycle.

In some embodiments, the clip and cardiac cycles are marked with respective clip and cardiac annotations, which indicate the start times of the heart cycles. The cardiac annotations may be generated by analyzing an electrocardiogram (ECG) signal, which is measured during the present heart mapping procedure, or using any other suitable method. The clip annotations may be similarly generated from an ECG signal (at the time of clip recording), or, for example, by analyzing the image frames of the fluoroscopic clip.

In an embodiment, the second synchronization stage is implemented by a cardiac correlator, which receives the annotations marking the current and previous cardiac and clip matching cycles. The cardiac correlator estimates the clip and cardiac HRs from the respective durations of the previous cycles, and estimates the cardiac and clip active phase duration using the non-linear function. The cardiac correlator then separately adapts the presentation times of the clip frames that belong to the active and passive phases.

In some embodiments, rendering events mark the times in which to update and display the 3D map of the heart. Upon receiving a rendering event, a clip frame whose adapted presentation time matches the received rendering time is selected and displayed (possibly registered and overlaid on the 3D map).

By applying non-linear time warping to the clip frames, taking into consideration the different dependence of the intra-cycle phases on the heartbeat rate, the disclosed techniques enable to play the fluoroscopic clip in synchronization with the present heartbeat rate and with little or no time distortions.

System Description

FIG. 1 is a schematic, pictorial illustration of a system 20 for intracardiac electrophysiological (EP) mapping, in accordance with an embodiment of the present invention. System 20 may be based, for example, on the above-mentioned CARTO system, with suitable additions to the system software. System 20 comprises a probe, such as a catheter 24, and a control console 34. In the embodiment described hereinbelow, catheter 24 is used in mapping a heart 26 of a patient 30. Alternatively, catheter 24 or other suitable probes may be used, mutatis mutandis, for other therapeutic purposes in the heart. For example, in some embodiments, the catheter is used for creating a 3D mapping of the heart, with or without performing an additional medical procedure, such as, for example cardiac ablation.

In the example system of FIG. 1, an operator 22, such as a cardiologist, inserts catheter 24 through the vascular system of patient 30 so that the distal end of the catheter enters a chamber (e.g., a ventricle or atrium) of heart 26. Catheter 24 is typically connected by a suitable connector at its proximal end to console 34. In alternative systems, means other than a catheter may also be used for dynamic cardiac mapping.

In this pictured embodiment, system 20 uses magnetic position sensing to determine position coordinates of the distal end of catheter 24 inside heart 26. For this purpose, a driver circuit 38 in console 34 drives field generators 32 to generate magnetic fields within the body of patient 30. Typically, field generators 32 comprise coils, which are placed below the patient's torso at fixed, known positions. These coils generate magnetic fields in a predefined working volume that contains heart 26. A magnetic field sensor (not shown) within the distal end of catheter 24 generates electrical signals in response to these magnetic fields. A signal processor 40 processes these signals in order to determine the position coordinates of the distal end of catheter 24, typically including both location and orientation coordinates. This method of position sensing is implemented in the above-mentioned CARTO system and is well known in the art. Alternatively or additionally, system 20 may use other methods of position sensing that are known in the art, such as ultrasonic or electrical impedance-based methods.

Processor 40 in console 34 typically comprises a general-purpose computer processor, with suitable front end and interface circuits for receiving signals from catheter 24 and for controlling and receiving inputs from the other components of console 34. Processor 40 may be programmed in software to carry out the functions that are described herein. The software may be downloaded to processor 40 in electronic form, over a network, for example, or it may be provided, alternatively or additionally, on tangible, non-transitory media, such as optical, magnetic or electronic memory media. Further alternatively or additionally, some or all of the functions of processor 40 may be carried out by dedicated or programmable digital hardware components.

Based on the signals received from catheter 24 and other components of system 20, processor 40 drives a display 42 to present operator 22 with a three-dimensional (3D) map 44 of heart 26. The map may indicate cardiac electrophysiological activity measured by catheter 24, as well as providing visual feedback regarding the position of the catheter in the patient's body and status information and guidance regarding the procedure that is in progress.

Processor 40 can additionally accept a previously recorded fluoroscopic or cine clip via a suitable interface and store the clip locally in a memory of processor 40 (the interface and memory are not shown). Operator 22 may configure console 34 (e.g., using controls 48 and on-screen menus) to play the clip and present it on display 42, possibly overlaid on map 44. The techniques that are disclosed herein enable playback of the fluoroscopic clip in synchronization with the heartbeat rate during the cardiac mapping procedure without time distortions.

Although FIG. 1 shows a particular system configuration and application environment, the principles of the present invention may similarly be applied in other therapeutic applications using not only catheters, but also probes of other types.

Dependence of Ventricular Volume Dynamics on Heartbeat Rate

Figure 2:
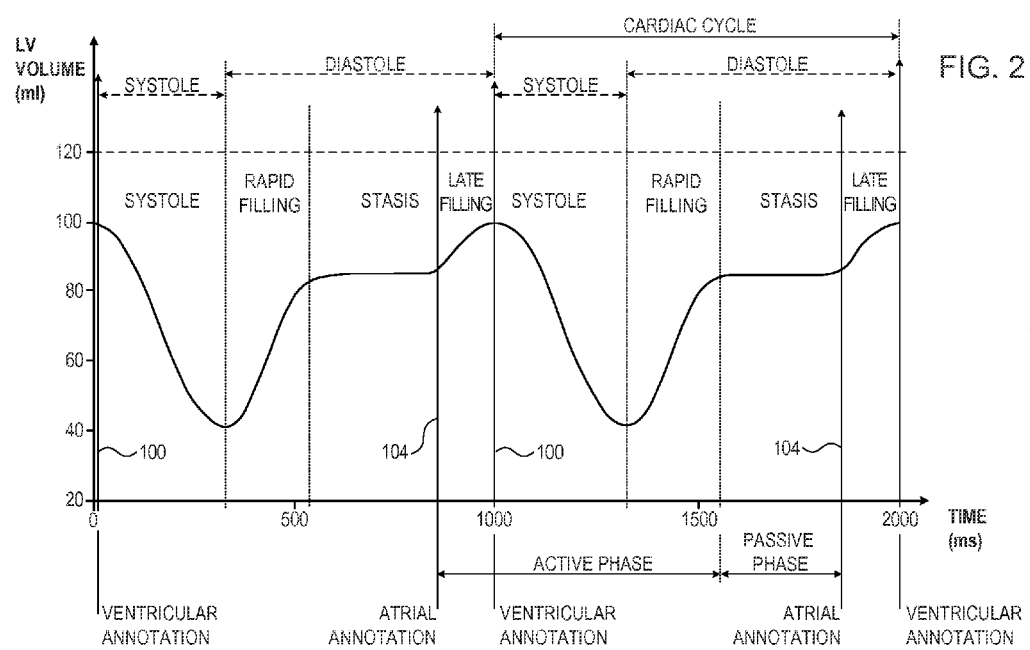
FIG. 2 is a graph showing a characteristic dynamic behavior of the heart ventricular volume, in accordance with an embodiment of the present invention.

FIG. 2 is a graph showing a characteristic dynamic behavior of the volume of the left ventricle (LV) of the heart, in accordance with an embodiment of the present invention. The graph in FIG. 2 is based on sampling real dynamic behavior of the heart at about 60 BPM, using 3D echocardiography. A heartbeat cycle comprises a systole phase in which the heart ventricles contract, and a diastole phase in which the ventricles relax. During the systole phase the volume of the ventricles decreases rapidly. The diastole phase can be further divided into three sub-phases referred to as rapid filling, stasis, and late filling phases. In the description that follows, the rapid filling phase is also referred to as an early filling phase.

During the early filling phase, at the beginning of the diastole phase, the ventricles start to relax and to fill up with blood, and therefore their volume increases rapidly. During the diastole stasis phase, the volume of the ventricles is typically constant, or changes at a low rate e.g., while passively filling. During the late filling phase of the diastole, the atria contract to further fill the ventricles and thus increase the ventricular volume relatively fast.

In the context of the present invention, the inventors have found it convenient to divide the cardiac cycle into two other phases, which are referred to herein as active and passive phases. The active phase comprises the late filling, systole, and early filling phases, and the passive phase comprises the stasis phase. As explained below with reference to FIG. 3, the respective durations of the active and passive phases depend differently on the heartbeat rate.

In some embodiments, the boundaries of the cardiac cycle are determined at the beginning of the systole phase when the ventricles are filled to their maximal volume. The marks of the systole phase starting times are referred to as ventricular annotations 100. In other embodiments, the cycle boundaries are determined at the beginning of the active phase and are marked by atrial annotations 104.

The dynamics of the volume of the left ventricle during the cardiac cycle as depicted in FIG. 2 is chosen purely for the sake of conceptual clarity, and the disclosed techniques are also applicable to other cardiac volume dynamics. As an example, the duration of each of the different cardiac phases may depend differently on the underlying heartbeat rate. Moreover, the configuration in which dividing the heart cycle into four phases as depicted in FIG. 2 is not mandatory and divisions into other phases are possible. For example in alternative embodiments, the cardiac cycle may be divided into a number of phases other than four and/or phases that are positioned differently along the cardiac cycle.

Clinical studies have demonstrated that the dependence of the duration of the active and passive phases on the heartbeat rate may be different. Moreover, the dependence differs between low and high heartbeat rates. For example, Chung et al. discuss the dependence of the diastolic sub-phases on the heartbeat rate, in "Duration of diastole and its phases as a function of heart rate during supine bicycle exercise," American Journal of Physiology—Heart and Circulatory Physiology, Nov. 1, 2004, volume 287, number H2003-H2008, which is incorporated herein by reference. As another example, Bombardini et al. investigate the systolic and diastolic times during stress, in "Diastolic time—frequency relation in the stress echo lab: filling timing and flow at different heart rates," Cardiovascular Ultrasound, Apr. 21, 2008, which is incorporated herein by reference.

Figure 7:
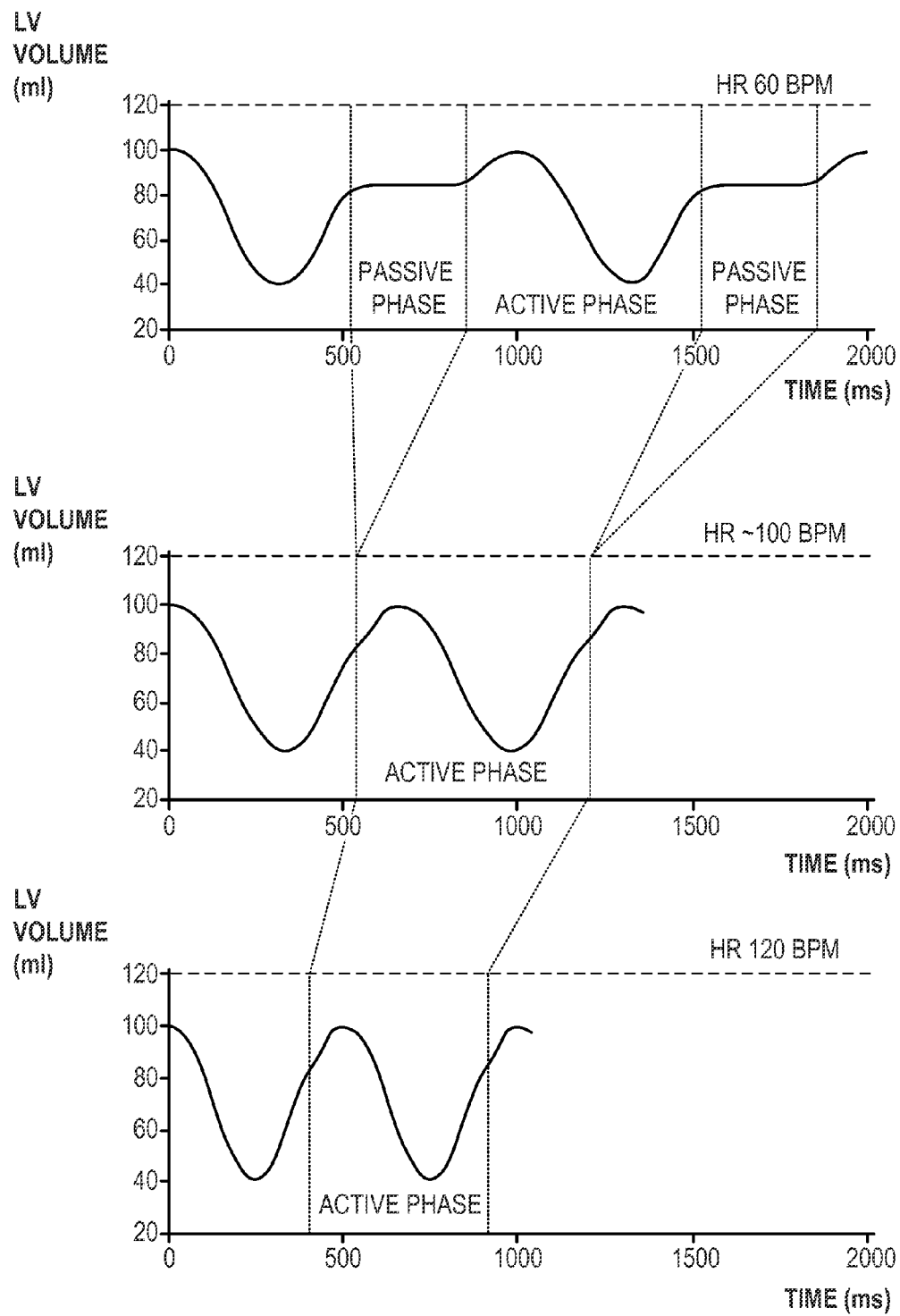
FIG. 7 is a graph depicting a characteristic dynamic behavior of the heart ventricular volume at three different heartbeat rates, in accordance with an embodiment of the present invention.

Based on the above cited (and other) references, the inventors have defined a threshold heartbeat rate, which approximately equals 100 beats per minute (BPM). Thus, at heartbeat rates below the threshold rate, the duration of the active phase is insensitive to the underlying heartbeat rate, and as the heartbeat rate increases the cardiac cycle period decreases mostly due to the respective decrease of the passive phase duration. When the heartbeat rate increases above the threshold rate, the stasis diastole phase vanishes, and the cardiac cycle period essentially equals the duration of the active phase alone. FIG. 7 below depicts an example dynamics of the volume of the left ventricle at 60, 100, and 120 BPM.

Figure 3:
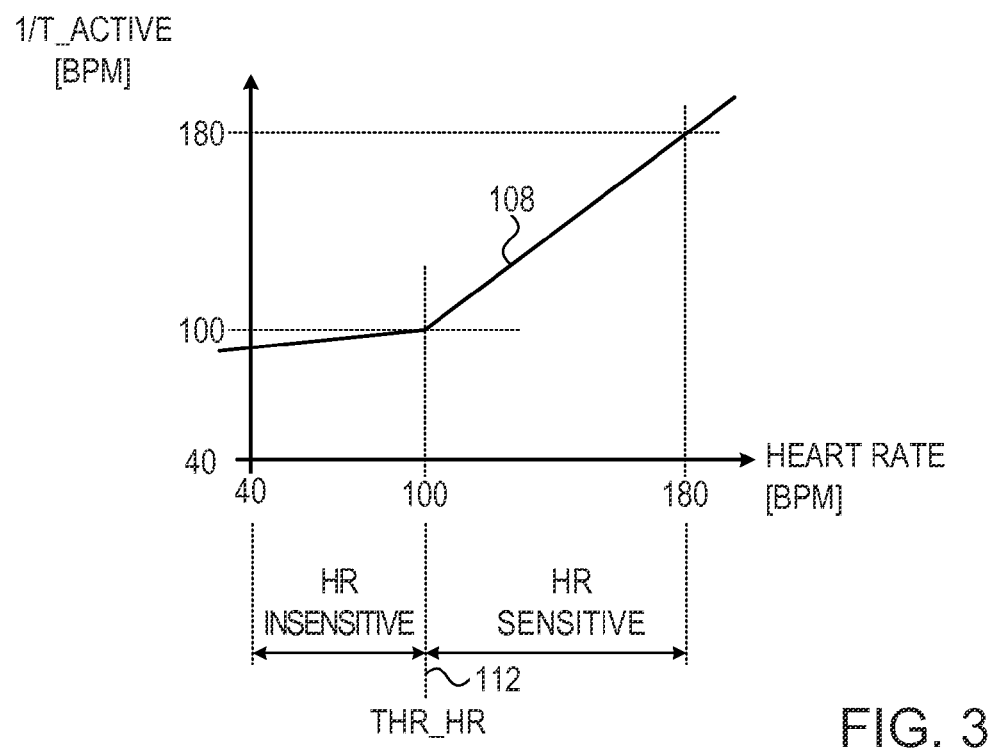
FIG. 3 is a graph depicting a non-linear function that relates between the duration of the active phase within the heart cycle and the heartbeat rate.

FIG. 3 is a graph depicting a non-linear function 108 that relates between the duration of the active phase within the heart cycle and the heartbeat rate. In the figure, the horizontal axis denotes heartbeat rates in the range of 40-180 BPM. The vertical axis denotes reciprocal values of the active phase duration (denoted T_ACTIVE) and therefore the values are given in units of BPM. The example function in FIG. 3 is piecewise linear and comprises two linear segments that correspond to heartbeat rates below and above a threshold rate 112 (denoted THR_HR). The segment of function 108 corresponding to heartbeat rates below THR_HR has a close to flat slope, indicating weak dependency of the active phase duration on the heartbeat rate in this zone. On the other hand, the slope of the segment that corresponds to heartbeat rates above THR_HR equals 1, as expected when the passive phase vanishes.

As an example of how the function of FIG. 3 can be used, consider a given heartbeat rate of 170 BPM. In this case the function maps the given heartbeat to 170 BPM, and the corresponding duration of the active phase would be 1/170 minutes or equivalently 60/170 seconds.

The configuration of function 108 in FIG. 3 is an exemplary configuration, and other suitable functions can also be used. For example, the threshold rate may correspond to a heartbeat rate other than 100 BMP, and the two linear segments may have other suitable slopes. Moreover, the function may comprise a piecewise linear function having more than two linear segments. Function 108 can also comprise a non-linear curve, or a combination of multiple linear and non-linear curves.

Cardiac Mapping System with Flouroscopic Clip Synchronization

As described above, when performing a medical procedure that involves cardiac mapping, it may be advantageous to display, in addition to the cardiac map, a previously recorded fluoroscopic clip of the same patient. To be valuable to the physician, the playback of the fluoroscopic clip should be synchronized to the present heartbeat rate without intra-cycle time distortions.

Figure 4:
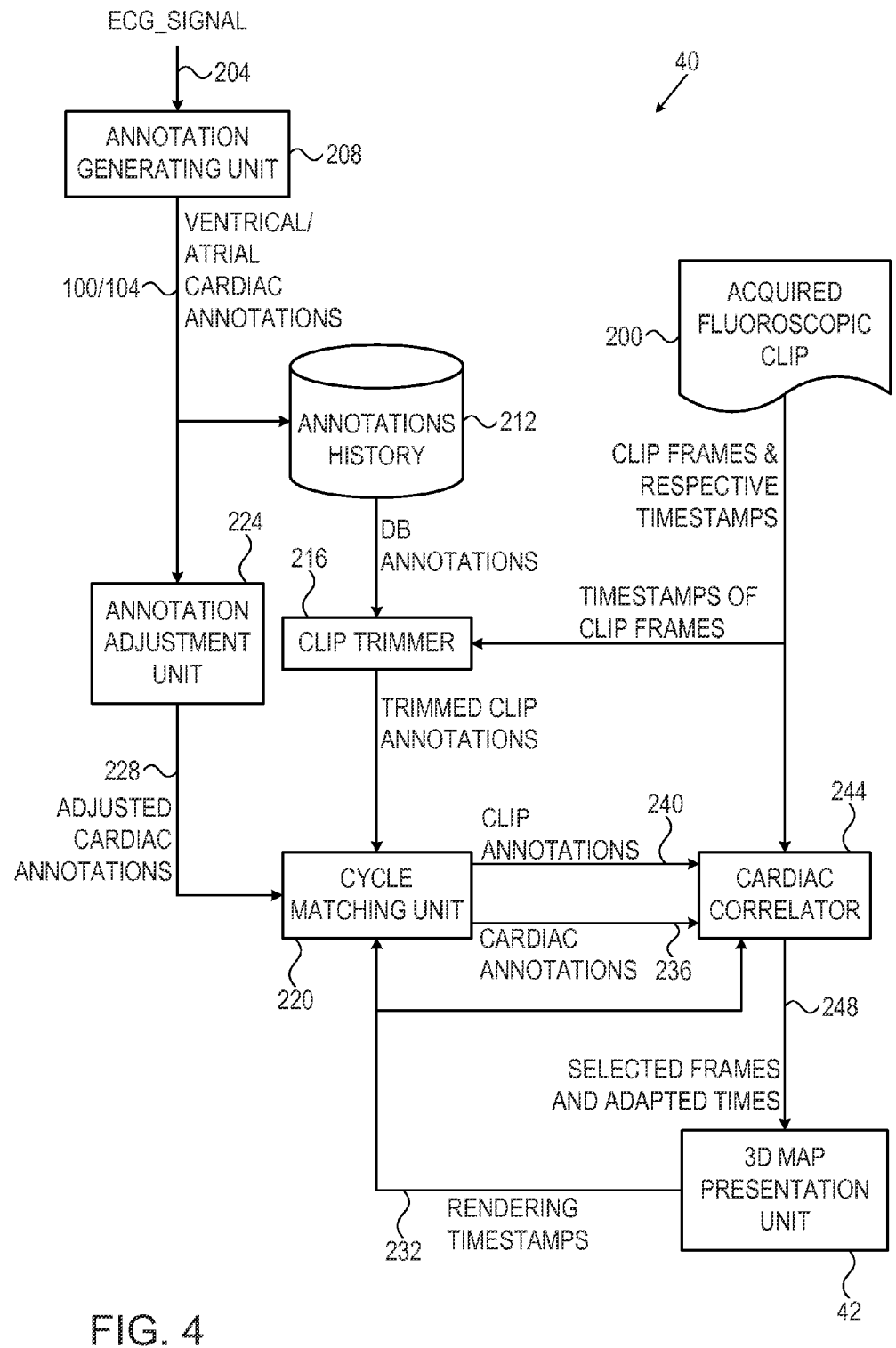
FIG. 4 is a block diagram that schematically illustrates a cardiac mapping system, including synchronization of a fluoroscopic clip to the present heartbeat rate.

FIG. 4 is a block diagram that schematically illustrates a cardiac mapping system 40, including synchronization of a fluoroscopic clip 200 to the present heartbeat rate. The system of FIG. 4 is typically implemented by processor 40 of console 34.

Processor 40 receives a fluoroscopic clip 200 showing the dynamic heart activity via a suitable interface (not shown). In some embodiments, fluoroscopic clip 200 is recorded for the same patient 30 before carrying out the present heart mapping. Clip 200 comprises a sequence of image frames each associated with a respective frame timestamp. Fluoroscopic clip 200 typically comprises a few tens of frames (e.g., 50-200 frames) having a frame rate of 25 frames per second (i.e., each frame is presented for about 40 milliseconds). Other typical frame rates for the fluoroscopic clip include 30, 15, 7.5, and 3.75 frames per second. The frame rate used in EP mapping is typically below 15 frames per second. Generally, however, any suitable frame rate can be used. In the example embodiment of system 40, the processor synchronizes the presentation of the clip frames to the present heartbeat rate in two main stages as described below.

In the description that follows the terms "clip cycles" and "clip annotations" refer to the heartbeat cycles and respective annotations that mark the cycle starting and ending times in the fluoroscopic clip. Similarly, the terms "cardiac cycles" and "cardiac annotations" refer to the heartbeat cycles and starting/ending markings during the present cardiac mapping operation.

In the first synchronization stage, processor 40 synchronizes between the cardiac and the clip cycles by matching the current cardiac cycle to one of the clip cycles. In the second synchronization stage, processor 40 performs time warping of the clip frames that occur during the matched clip cycle to be aligned with the current cardiac cycle.

Processor 40 can use any suitable method to synchronize between the cardiac and clip cycles. In the present embodiment, processor 40 performs cycle synchronization based on electrocardiography signal (denoted ECG_SIGNAL) 204 that is measured using suitable equipment (not shown) during and in addition to the cardiac mapping procedure. An annotation generating unit 208 analyzes ECG_SIGNAL 204 to determine cardiac ventricular annotations 100, cardiac atrial annotations 104, or both. As explained above, the ventricular and atrial annotations comprise the time instances in which the systole and active phases start, respectively.

Processor 40 may use any suitable method for locating the ventricular/atrial annotations. In an example embodiment, processor 40 estimates the time instances of the ventricular and/or atrial annotations by locating local peaks in ECG_SIGNAL 204. In alternative embodiments, processor 40 can use any other suitable means, possibly based on measurements other than ECG, to generate the annotations.

Processor 40 stores the cardiac annotations generated by annotation generating unit 208 as DB annotations in an annotation history database (DB) 212. Processor 40 can associate DB annotations with fluoroscopic clip 200, for example, based on the time at which the clip was recorded. In some embodiments, processor 40 or some other processor or subsystem of system 20 performs the recording of fluoroscopic clip 200 and determines the ventricular and/or atrial annotations corresponding to the clip. In such embodiments, processor stores the annotations of the clip in DB 212 in association with the respective fluoroscopic clip.

A clip trimmer 216 accepts DB annotations stored in DB 212, and frame timestamps of fluoroscopic clip 200. Clip trimmer 216 selects a subset of the clip frames and associates the instances of the DB annotations with the timestamps of the respective selected frames. Additionally, clip trimmer 216 trims the clip by discarding clip frames whose timestamps precede the earliest annotation within the clip or occur following the latest annotation within the clip. The output of clip trimmer 216 thus comprises a sequence of annotation time instances corresponding to multiple non-fractional clip cycles of the fluoroscopic clip.

In alternative embodiments, instead of discarding frames, trimmer 216 appends black or transparent frames at the beginning and/or end of the clip to complete the missing parts of the first and last cycles respectively. The appended frames are displayed when the clip is played cyclically.

In yet other alternative embodiments, selected frames at the beginning and end parts of the clip (not necessarily with alignment to any annotations) are trimmed, so that the frames of the first and last fractional cycles appear as a complete cycle when the clip is played cyclically.

An annotation adjustment unit 224, receives ventricular, atrial, or both annotations from annotation generating unit 208 (or from DB 212), and outputs adjusted cardiac annotations, i.e., either atrial or ventricular cardiac adjusted annotations 228. In some embodiments, processor 40 translates ventricular into atrial annotations (e.g., when the atrial annotations are not available) by subtracting suitable time durations from the time instances of the ventricular annotations. Similarly, processor 40 translates atrial annotations into ventricular annotations by adding suitable time durations. The subtracted or added time durations may correspond, for example, to instantaneous or average PR interval of ECG_SIGNAL 204, or computed as a fixed fraction of the duration of the active phase.

A cycle matching unit 220 receives clip annotations of the trimmed clip from trimmer 216, and atrial or ventricular adjusted annotations 228 from unit 224. Each clip or cardiac cycle is marked by respective two consecutive clip or cardiac annotations. Cycle matching unit 220 further receives rendering timestamps 232 from 3D map presentation unit 42. Rendering timestamps 232 are the time instances in which processor 40 renders an updated version of 3D map 44 of heart 26.

Cycle matching unit 220 matches cardiac cycles that are marked by cardiac annotations 228, to respective clip cycles marked by clip annotations output by clip trimmer 216. In an embodiment, upon receiving a rendering event timestamp 232, cycle matching unit 220 counts the number of cardiac annotations 228 received by unit 220 since the previous rendering event. Typically, unit 220 counts a number of zero or one annotations, and advances to the next clip cycle in fluoroscopic clip 200 accordingly (i.e., only when the number of annotations in positive).

Alternatively, cycle matching unit 220 counts multiple annotations that have occurred since the previous rendering time, for example, when the computation resources of the processor where temporarily insufficient, and unit 220 advances multiple clip cycles in the fluoroscopic clip accordingly.

Processor 40 cyclically advances over the trimmed clip cycles. In other words, if when transitioning to the next clip cycle processor 40 passes over the last clip cycle, the processor wraps around to the first clip cycle.

In alternative embodiments, processor 40 matches between the cardiac and clip cycles by calculating, for example, correlation values between the cardiac and trimmed clip cycle durations, or by using any other suitable method.

Cycle matching unit 220 outputs cardiac annotations 236 that correspond to the current and previous cardiac cycles, and clip annotations 240 that correspond to the respective matching current and previous clip cycles.

A cardiac correlator 244 receives fluoroscopic clip 200 (i.e., the clip's frames and respective timestamps) and outputs selected frames 248 having respective presentation time instances. Cardiac correlator 244 operates at the cycle level. Given a cardiac cycle and a matching clip cycle, the correlator performs non-uniform time warping of the clip frames within the current clip cycle to be aligned with the current cardiac cycle without introducing time distortions among the frames. Processor 40 divides each of the clip and cardiac cycles into active and passive phases and performs separate time adjustments to the clip frames in each of the active and passive phases.

Processor 40 estimates the respective heartbeat rates of the current clip and cardiac cycles, for example, by calculating the reciprocal of the respective previous cycle periods. Processor 40 uses the estimated heartbeat rates and function 108 (of FIG. 3) to derive the active phase duration for the current cardiac and clip cycles. The processor then calculates the passive phase durations by subtracting the estimated active phase duration from the estimated cycle period.

Processor 40 then determines the presentation time of the clip frames by performing separate time adjustment over the active and passive phases. Typically, processor 40 performs linear time adjustment to each of the active and passive phases. Alternatively, however, the processor may perform any other suitable time warping, such as, for example, non-linear time warping. For example, processor 40 can perform time warping so that the presentation times of the frames match the expected rendering instances 232. Note that when the estimated heartbeat rate exceeds THR_HR 112, the passive phase of the cycle vanishes. In FIGS. 5A-5D, we describe several time warping examples that take into account the heartbeat rate value relative to THR_HR 112.

In some embodiments, processor 40 renders an updates 3D map 44 with an overlaid clip frame whose determined presentation time is the closest to the current rendering time 232. In alternative embodiments, processor 40 presents the clip frames on display 42 (or some other display of system 20) separately from 3D map 44.

Time Warping of Flouroscopic Clip Frames

As described above, the second synchronization stage comprises time warping of the clip frames that occur within the currently matched clip cycle to be aligned with the current cardiac cycle. In contrast to conventional time warping methods that employ linear time adjustment over the entire heart cycle, the disclosed techniques employ non-linear time warping based on the non-linear dependency of the duration of the active phase on the heartbeat rate as described in FIG. 3 above.

FIGS. 5A-5D are diagrams showing four examples of time warping of a fluoroscopic clip frames within a single heart cycle. In the figures, CLIP_HR denotes the heartbeat rate at the time the fluoroscopic clip was recorded. MAP_HR1 and MAP_HR2 denote two values of the present heartbeat rate (e.g., during a heart mapping procedure). In the present example, MAP_HR2 is lower than MAP_HR1.

In the figures, CLIP_ACT and CLIP_PSV denote the respective active and passive phases of the clip cycles. Similarly, MAP_ACT1, MAP_PSV1, MAC_ACT2, and MAP_PSV2, denote the active and passive phases during the present heart mapping (referring to MAP_HR1 and MAP_HR2 respectively).

Figure 5A:
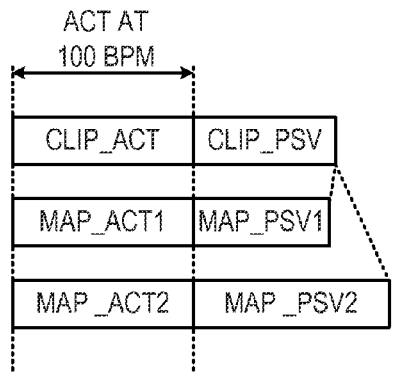
FIGS. 5A-5D are diagrams showing four examples of time warping of a fluoroscopic clip frames within a single heart cycle.
Figure 5B:
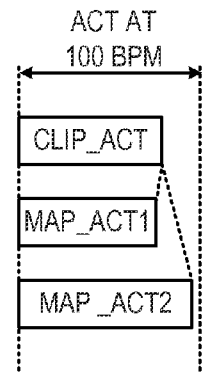

As seen in the figures, since according to function 108, below heartbeat rates of 100 BPM the duration of the active phase does not depend (or weakly depends) on the heartbeat rate, the active phases CLIP_ACT, MAP_ACT1 and MAP_ACT2 in FIG. 5A, as well as MAP_ACT1 in FIG. 5C, all have a duration similar to the duration of the active phase at 100 BPM. Additionally, in FIGS. 5B and 5D, the heartbeat rate exceeds 100 BPM causing the passive phase to vanish and the active phase to shorten.

Processor 40 determines the presentation time of the clip frames that occur during the CLIP_ACT phase to match the duration of the MA_ACT1 or MAP_ACT2 phase. Similarly, processor 40 separately determines the presentation time of the clip frames that occur during the CLIP_PSV phase to cover the duration of the MAP_PSV1 or MAP_PSV2 phase.

Figure 5C:
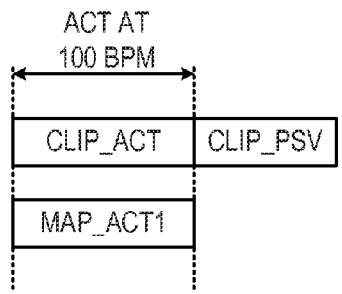
Figure 5D:
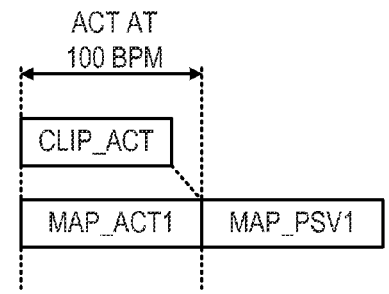

Note that in FIG. 5C CLIP_HR<100 BPM<MAP_HR1, and the phase MAP_PSV1 is missing. Similarly in FIG. 5D, MAP_HR1<100 BPM<CLIP_HR and the phase CLIP_PSV is missing. In these two cases processor 40 time warps only the clip frames of the respective active phases.

Figure 6:
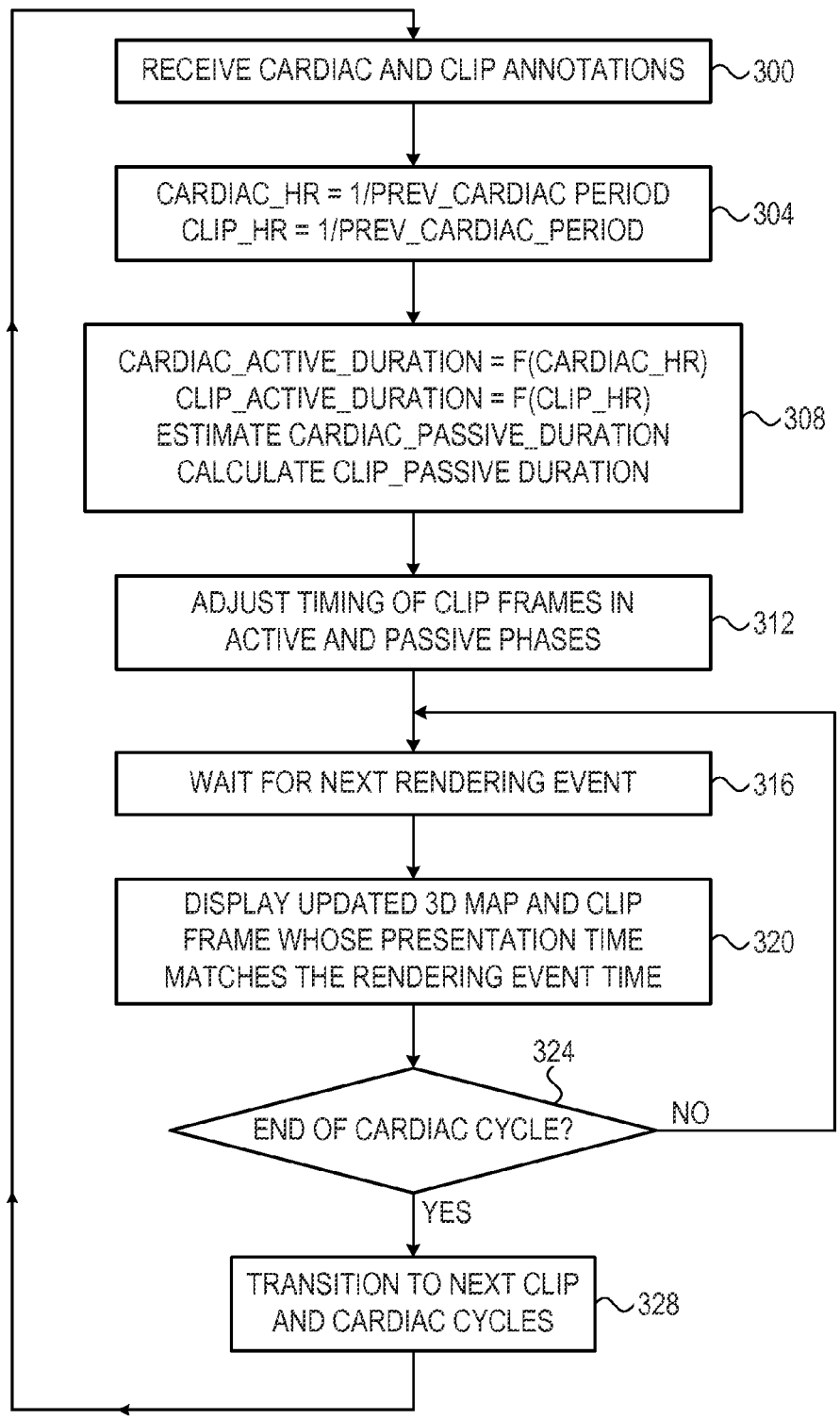
FIG. 6 is a flow chart that schematically illustrates a method for synchronizing a fluoroscopic clip to an EP map, in accordance with an embodiment of the present invention.

FIG. 6 is a flow chart that schematically illustrates a method for synchronizing a fluoroscopic clip to an EP map, in accordance with an embodiment of the present invention. The method begins with processor 40 receiving cardiac and clip annotations (e.g., annotations 236 and 240 produced by cycle matching unit 220), at an annotations reception step 300. The received annotations define the boundaries of the current and previous synchronized cardiac and clip cycles. At an estimation step 304, processor 40 estimates the cardiac and clip heartbeat rates by calculating the reciprocal of the duration of the previous cardiac and clip cycles. This estimation is needed since the duration of the current cycle is typically not available in real time.

In alternative embodiments in which, for example, the synchronization is carried out off-line, processor 40 may skip step 304 and use the current cycle duration.

At a phase duration estimation step 308, processor 40 calculates the active phase duration of the current cardiac and clip cycles. Processor 40 calculates the active phase duration, for example, by inputting the estimated heartbeat rates from step 304 into non-linear function 108. Further at step 308, processor 40 calculates the duration of each of the passive cardiac and clip phases by subtracting the estimated active phase duration from the respective cycle period. Note that the duration of the active phase, which is estimated using the previous cycle duration at step 304, should be limited below the actual duration of the current cycle (marked by the next annotation).

At a time warping step 312, processor 40 adjusts the presentation times of the clip frames during the current clip cycle along the duration of the current cardiac cycle. The processor performs non-linear time warping using, for example, the methods described in FIGS. 5A-5D above.

At a waiting step 316, processor 40 waits for the occurrence of a rendering event upon which the processor updates 3D map 44. At a display step 320, processor 40 displays the updated 3D map 44 and a clip frame whose presentation time is the closest to the current rendering time. In some embodiments, processor 40 displays the clip frame overlaid on the 3D map.

At a cycle termination step 324, processor 40 checks whether the cardiac cycle has ended. Processor 40 can detect that the cardiac cycle has ended, for example, by detecting a cardiac annotation whose time is later than the time of the last rendering event. If at step 324 the cardiac cycle has not yet ended, the processor loops back to step 316 to wait for subsequent rendering events. Otherwise, processor 40 transitions to the next clip and cardiac cycles, at a cycle transition step 328. Then processor 40 loops back to step 300 to receive subsequent cardiac and clip annotations. In some embodiments, the rendering events trigger the initiation of the processing operations described in FIG. 3.

FIG. 7 is a graph depicting a characteristic dynamic behavior of the volume of the left ventricle of the heart at three different heartbeat rates, in accordance with an embodiment of the present invention. The upper part of the figure depicts the dynamics of the ventricular volume at 60 BPM similarly to FIG. 2 above. In the upper part the cardiac cycle comprises both an active phase and a passive phase.

As described in FIG. 2 above, as the heartbeat rate increases towards a threshold rate of about 100 BPM, the duration of the passive phase gradually shortens. The middle part of FIG. 7 depicts the ventricular volume at about 100 BPM. As seen in the figure, at 100 BPM the passive phase vanishes, and the cardiac cycle comprises only the active phase.

At the bottom part of FIG. 7, the heartbeat rate further increases to 120 BPM. In this case, the cardiac cycle still comprises only the active phase whose duration is shorter compared to heartbeat rates up to 100 BPM.

The dynamics of the ventricular volume shown in FIG. 7 is exemplary, and other dynamics are also possible. For example, in a heart of another subject, the threshold heartbeat rate in which the passive phase vanishes may occur at a heartbeat rate other than 100 BPM.

The disclosed techniques described above are exemplary, and other suitable techniques can also be used. For example, in the method of FIG. 6 above, instead of estimating the heartbeat rate based on the duration of the previous heart cycle, the estimation can be based on an average duration over multiple previous cycles.

In the disclosed techniques an image sequence of a previously recorded clip is played in synchronization with the heartbeat rate during real-time heart imaging procedure that generates another image sequence. In alternative embodiments, each of these two image sequences can be previously recorded. In some embodiments, instead of playing one image sequence in synchronization with the heartbeat rate corresponding to another image sequence, both image sequences are played in synchronization with a given third heartbeat rate, which serves as a common reference rate.

Further additionally or alternatively, the disclosed techniques can be extended to simultaneously synchronize the playback of multiple previously recorded clips to the present heartbeat rate, or to a given common heartbeat rate.

In the disclosed embodiments, dividing the cardiac cycle into two or more phases (e.g., active and passive phases) corresponds to the dynamic behavior of the ventricular volume during the cycle. Alternatively or additionally, the cardiac cycle may be divided into two or more phases based on the dynamic behavior of the atrial volume. In other words, the disclosed techniques can be used to synchronize to the dynamic volume of any cardiac chamber.

Although in the disclosed techniques the synchronized fluoroscopic clip is presented on a display device, in alternative embodiments the synchronized clip, and possibly also the 3D map, are sent to an output device, such as for example, a memory device or database.

Although the embodiments described herein mainly address the application of fluoroscopy in EP procedures, the methods and systems described herein can also be used in other applications, such as in other cardiac diagnostic or interventional procedures, or in other clinical settings of different imaging modalities, such as various 2D or 3D echocardiography, Magnetic Resonance (MR), or stress echocardiography (e.g., ultrasound based).

It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method for performing a medical procedure, comprising:
holding a non-linear dependence between a duration of a given phase within a cardiac cycle and a respective heartbeat rate;
receiving first and second image sequences of a dynamic activity of a heart of a patient, acquired at respective different first and second heartbeat rates of the heart;
synchronizing between the first and second image sequences based on the non-linear dependence, on the first and second heartbeat rates, and on a given common heartbeat rate; and
playing the first and second image sequences in synchronization with the common heartbeat rate.

2. The method according to claim 1, wherein the common heartbeat rate equals the second heartbeat rate, wherein synchronizing between the first and second image sequences comprises synchronizing the second image sequence to the first image sequence, and wherein playing the first and second image sequences comprises playing the second image sequence in synchronization with the first heartbeat rate.

3. The method according to claim 1, wherein the given phase comprises an active phase, in which a volume of a chamber of the heart changes rapidly, and wherein holding the non-linear dependence comprises holding a non-linear function that relates the duration of the active phase to the respective heartbeat rate.

4. The method according to claim 3, wherein the cardiac cycle further comprises a passive phase in which the volume of the chamber of the heart changes slowly, and wherein synchronizing between the first and second image sequences comprises determining presentation times of images of the second image sequence in each of the active and passive phases based on the non-linear function.

5. The method according to claim 1, wherein holding the non-linear function comprises holding a piecewise linear function comprising two or more linear segments.

6. The method according to claim 5, wherein the piecewise linear function comprises first and second linear segments corresponding to respective heartbeat rates below and above a threshold heartbeat rate.

7. The method according to claim 4, wherein playing the second image sequence comprises selecting an image of the second image sequence whose determined presentation time matches a rendering time of a rendered image among the images of the first sequence.

8. The method according to claim 7, wherein playing the second image sequence comprises displaying the selected image of the second image sequence overlaid on the rendered image of the first image sequence.

9. The method according to claim 1, wherein receiving the first image sequence comprises receiving a dynamic real-time imaging of the heart.

10. The method according to claim 1, wherein receiving the second image sequence comprises receiving a previously recorded fluoroscopic clip.

11. The method according to claim 1, wherein the cardiac cycle comprises multiple sub-phases, the sub-phases correspond to respective multiple non-linear dependences that each relates between a duration of the respective sub-phase and the respective heartbeat rate, and wherein synchronizing between the first and second image sequences comprises determining presentation times of images of the first and second image sequences based on the multiple non-linear dependences, on the first and second heartbeat rates, and on the common heartbeat rate.

12. Apparatus for performing a medical procedure, comprising:
an output device; and
a processor, which is configured to hold a non-linear dependence between a duration of a given phase within a cardiac cycle and a respective heartbeat rate, to receive first and second image sequences of a dynamic activity of a heart of a patient, acquired at respective different first and second heartbeat rates of the heart, to synchronize between the first and second image sequences based on the non-linear dependence, on the first and second heartbeat rates and on a given common heartbeat rate, and to play the first and second image sequences synchronized to the common heartbeat rate on the output device.

13. The apparatus according to claim 12, wherein the common heartbeat rate equals the second heartbeat rate, and wherein the processor is configured to synchronize between the first and second image sequences by synchronizing the second image sequence to the first image sequence, and to play the second image sequence in synchronization with the first heartbeat rate.

14. The apparatus according to claim 12, wherein the given phase comprises an active phase, in which a volume of a chamber of the heart changes rapidly, and wherein the processor is configured to hold a non-linear function that relates the duration of the active phase to the respective heartbeat rate.

15. The apparatus according to claim 14, wherein the cardiac cycle further comprises a passive phase in which the volume of the chamber of the heart changes slowly, and wherein the processor is configured to synchronize between the first and the second image sequences by determining presentation times of images of the second image sequence in each of the active and passive phases based on the non-linear function.

16. The apparatus according to claim 12, wherein the processor is configured to hold a piecewise linear function comprising two or more linear segments.

17. The apparatus according to claim 16, wherein the piecewise linear function comprises first and second linear segments corresponding to respective heartbeat rates below and above a threshold heartbeat rate.

18. The apparatus according to claim 15, wherein the processor is configured to play the second image sequence by selecting an image of the second image sequence whose determined presentation time matches a rendering time of a rendered image among the images of the first image sequence.

19. The apparatus according to claim 18, wherein the processor is configured to play the second image sequence by displaying the selected image of the second image sequence overlaid on the rendered image of the first image sequence.

20. The apparatus according to claim 12, wherein the processor is configured to receive the first image sequence by receiving a dynamic real-time imaging of the heart.

21. The apparatus according to claim 12, wherein the processor is configured to receive the second image sequence by receiving a previously recorded fluoroscopic clip.

22. The apparatus according to claim 12, wherein the cardiac cycle comprises multiple sub-phases, the sub-phases correspond to respective multiple non-linear dependences that each relates between a duration of the respective sub-phase and the respective heartbeat rate, and wherein the processor is configured to synchronize between the first and second image sequences by determining presentation times of images of the first and second image sequences based on the multiple non-linear dependences, on the first and second heartbeat rates, and on the common heartbeat rate.

* * * * *